United States Patent [19]
Bourdin et al.

[11] Patent Number: 6,114,300
[45] Date of Patent: Sep. 5, 2000

[54] SPIROCYCLIC COMPOUNDS

[75] Inventors: Bernadette Bourdin, Dübendorf; Georg Fráter, Winterthur; Jerzy A. Bajgrowicz, Zürich, all of Switzerland

[73] Assignee: Givaudan Roure (International) SA, Geneva, Switzerland

[21] Appl. No.: 09/182,853

[22] Filed: Oct. 29, 1998

[30] Foreign Application Priority Data

Oct. 29, 1997 [EP] European Pat. Off. .............. 97810805

[51] Int. Cl.$^7$ ........................... A61K 7/46; C07C 49/105
[52] U.S. Cl. .................. 512/9; 552/24; 552/27; 568/367; 568/376; 568/379
[58] Field of Search .................. 512/22, 24, 20, 512/21, 9, 27; 568/343, 345, 347, 349, 361, 367, 376, 379

[56] References Cited

U.S. PATENT DOCUMENTS

| | | | |
|---|---|---|---|
| 4,147,672 | 5/1979 | Schulte-Elte et al. | 252/522 |
| 4,264,467 | 4/1981 | Schulte-Elte et al. | 252/174.11 |
| 4,281,204 | 7/1981 | Willis et al. | 568/361 |
| 4,289,659 | 9/1981 | Schulte-Elte et al. | 252/522 R |

FOREIGN PATENT DOCUMENTS 2 259 091 of 1975 France .
2 021 574 of 1979 United Kingdom .

OTHER PUBLICATIONS

Morris, A.F., *Perfumer & Flavorist*, v. 16:33–35 (1991).
Wender, P.A., et al. *Org. & Synthesis*, v. 70:204–214 (1992).
Saucy, R., *Helvetica Chimica Acta*, v. 50:2091–2095 (1967).

*Primary Examiner*—Johann Richter
*Assistant Examiner*—Sreeni Padmanabhan
*Attorney, Agent, or Firm*—Mark E. Waddell; Stephen M. Haracz; Bryan Cave LLP

[57] ABSTRACT

Spirocyclic compounds of the general formula (I) are provided which are powerful odorants. Compositions which include these compounds are also provided. They can be used, for instance, in perfumery.

10 Claims, No Drawings

SPIROCYCLIC COMPOUNDS

FIELD OF THE INVENTION

The present invention relates to spirocyclic compounds that are powerful odorants and that are useful, for instance, in perfumery. The invention also concerns fragrance compositions containing one or more of these spirocyclic compounds.

BACKGROUND OF THE INVENTION 1-(5,5-dimethyl-1-cyclohexen-1-yl)-4-penten-1-one is described by Morris, A. F.; Näf, F.; Snowden, R. L. in Perfumer & Flavorist 1991, 16, 33 as a very important raw material in perfumery that gives unique fresh, green, floral and fruity effects to perfumes. The high performance that has made the success of this raw material is due to an ideal profile: outstanding diffusion, high tenacity in application, excellent stability combined with a unique powerful metallic odour reminiscent of galbanum, with a pineapple and hyacinth character.

SUMMARY OF THE INVENTION

The present invention relates to new spirocyclic compounds of the general formula I

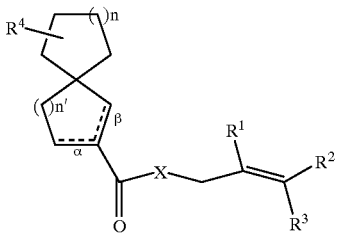

in which the —C(O)X-substituted ring is saturated or unsaturated in the α or β position and wherein:

X represents a methylene group or an oxygen atom, $R^1$, $R^2$, $R^3$, $R^4$ are independently a hydrogen atom or a methyl radical, n and n' are independently 1 or 2, $R^4$ can be at any position on the ring not being the —C(O)X substituted ring.

The formula includes all different possible stereoisomers.

The spirocyclic compounds of the present invention have fresh, metallic, green-galbanum and fruity-pineapple odours. Fragrance compositions including one or more of these spirocyclic compounds are also provided.

An object of the present invention is to provide new compounds with the advantages of 1-(5,5-dimethyl-1-cyclohexen-1-yl)-4-penten-1-one. It is also an object to provide compounds with enhanced substantivity as compared to this perfumery compound.

DETAILED DESCRIPTION OF THE INVENTION

The present invention relates to new spirocyclic compounds of the general formula I

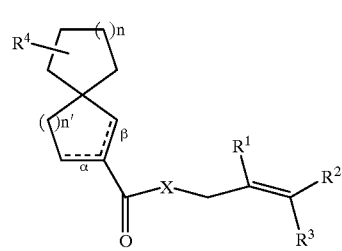

in which the —C(O)X-substituted ring is saturated or unsaturated in the α or β position and wherein:

X represents a methylene group or an oxygen atom, $R^1$, $R^2$, $R^3$, $R^4$ are independently a hydrogen atom or a methyl radical, n and n' are independently 1 or 2, $R^4$ can be at any position on the ring not being the —C(O)X substituted ring.

The formula includes all different possible stereoisomers.

The spirocyclic compounds of the present invention have fresh, metallic, green-galbanum and fruity-pineapple odours.

It has surprisingly been found that the replacement of the gem-dimethyl substituents by a ring strongly enhances the substantivity (persistence of the odour) of the product without changing the perception and type of odour. The difference in substantivity is well observed on a smelling strip: the new spirocyclic odorants of formula I are perceived longer and still with high intensity. This is also the case on fabrics washed with a detergent or treated with a softener perfumed with the new spirocyclic odorant: the typical fresh green odour is perceived still on the dry fabric whereas this is not the case for the gem-dimethyl analogue.

The new spirocyclic compounds show, at the same time enhanced substantivity and a green, fresh and fruity odour and are therefore specially suitable and advantageous for use in any domain of fine and functional perfumery (household products, laundry and beauty care). They are particularly advantageous for laundry products (detergents, softeners) perfumery where the finding of highly substantive fragrances is still a challenge.

The new spirocyclic odorant molecules of the invention can be prepared from the corresponding spiroketones according to the process illustrated by Scheme 1 below (This process is described more in details in Example 1.). The starting spiroketone can be prepared according to Wender, P. A.; White, A. W.; McDonald, F. E. Org. Synthesis 1992, 70, 204.

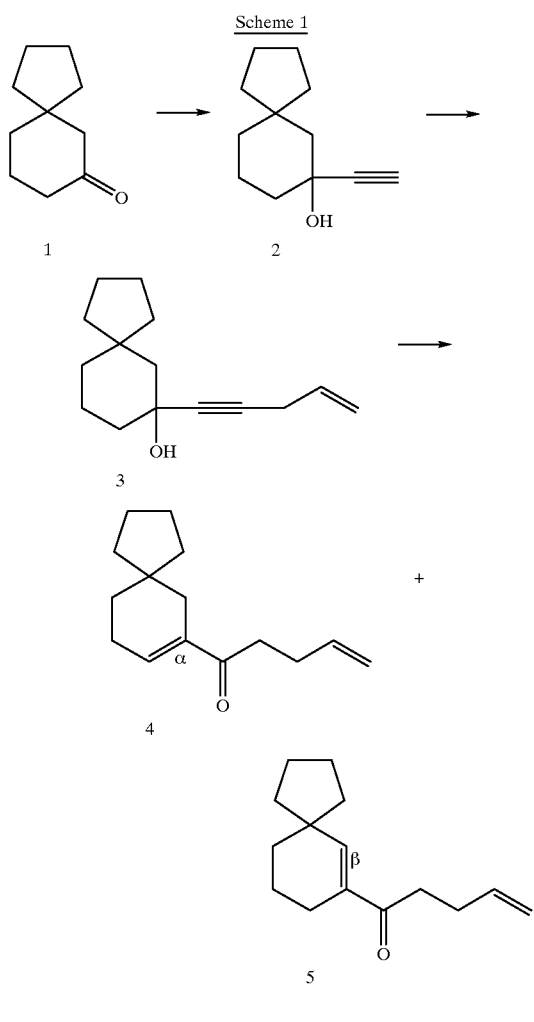

Scheme 1

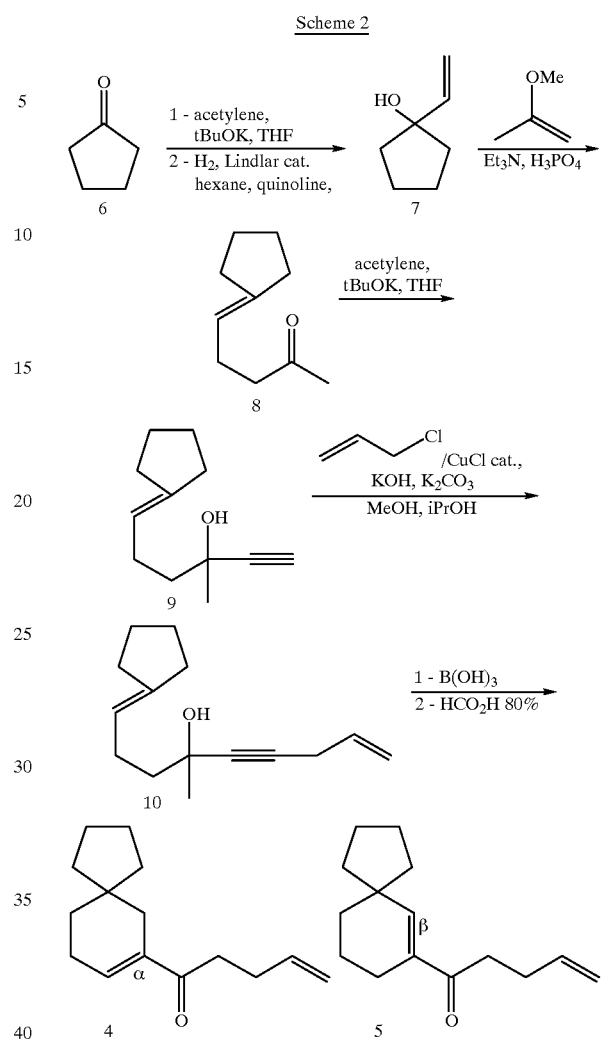

Scheme 2

This process which is used for compounds with different ring sizes yields a mixture of isomers α and β in a ratio α/β varying from ~2/1 to ~1/2 depending on the size of the rings. In all cases, the α-isomer is the most powerful and valuable odorant with an extraordinarily low odour threshold of ~15 pg/l (the spirononane and spirodecane derivatives being stronger than the higher homologs) combined with the metallic green-galbanum and fruity-pineapple odour character. In comparison, the β-isomer is less odorant and has more floral character, accompanied in some cases by additional fresh (minty, anisic) and persistent notes creating a beautiful fresh green accord together with the α-isomer.

Interestingly, in some cases, the published procedure for the synthesis (U.S. Pat. No. 4,264,467) of the gem-dimethyl analogue starting from dehydrolinalool was found to be also a possible synthetic route to the new spirocyclic odorants, what is illustrated below by scheme 2. In this case, the dehydrolinalool analogue (9) was synthesized from cyclopentanone in a few steps including a Saucy-Marbet reaction (G. Saucy; R. Marbet in Helvetica Chimica Acta 1967, 50, 2091) as the key-step.

Scheme 2

The new odorants, claimed herein, may be combined with numerous known odorant ingredients of natural and/or synthetic origin, whereby the range of the natural odorants can include not only readily volatile, but also moderately and difficultly volatile components, and the synthetic ones can embrace representatives from practically all classes of substances. The following list comprises examples of known odorants which may be combined with the compounds of the invention:

Natural products: such as tree moss absolute, basil oil, tropical fruit oils (such as bergamot oil, mandarin oil, etc.), mastix absolute, myrtle oil, palmarosa oil, patchouli oil, petitgrain oil, wormwood oil, lavender oil, rose oil, jasmin oil, ylang-ylang oil, etc.;

Alcohols: such as farnesol, gerniol, linalool, nerol, phenylethylalcohol, rhodinol, cinnamic alcohol, cis-3-hexenol, menthol, α-terpineol, etc.;

Aldehydes: such as citral, α-hexyl cinnamaldehyde, Lilial® (Givaudan Roure), hydroxycitronellal, methylnonylacetaldehyde, phenylacetaldehyde, anisaldehyde, vanillin, etc.;

Ketones: such as allylionones, α-ionone, β-ionone, Isoraldeine® (Givaudan Roure), methylionone, verbenone, nootkatone, geranylacetone, etc.;

Esters: such as allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate, etc;

Lactones: such as γ-undecalactone, δ-decalactone, pentadecanolide, 12-oxahexadecanolide, etc.;

Acetals: such as Viridine (phenylacetaldehyd dimethyl acetal), etc;

Various components: often used in perfumery such as indole, p-mentha-8-thiol-3-one, methyleugenol, eugenol, anethol, etc.

The novel odorants harmonise particularly well with all floral notes (lily of the valley, rose, iris, jasmine, ylang-ylang, narcissus notes, etc.), as well as with woody, chypre and animalic notes, tobacco like and patchouli compositions, etc.

The percentages in which they are used in compositions may vary within wide limits ranging from a few parts per thousand in mass market products (e.g. cleaning, deodorant) up to a few percent in alcoholic extracts for (fine) perfumery. In all cases, even in small amounts, they provide odorant compositions with intense fresh green-fruity notes and increase the volume (strength, diffusivity) and substantivity of their odour. In particular, the manner in which they extend the olfactory duration of the composition is remarkable.

There is really no restriction regarding the type of formulations and the destination of the actual finished product: thus, eau de cologne, toilet water, scented water, perfume, cream, shampoo, deodorant, soap, detergent powder, household cleaner, softener, etc., come into consideration.

Convenient methods for preparing the compounds of the invention are outlined in the examples without limiting the invention thereto.

EXAMPLE 1

1-(Spiro[4.5]dec-7-en-7-yl)-pent4-en-1-one(4) and 1-(spiro[4.5]dec-6-en-7-yl)-pent-4-en-1-one(5 a) 7-Ethynyl-spiro[4.5]decan-7-ol (2)

Acetylen was bubbled for 30 mn through a mixture of tBuOK (14.11 g, 125.8 mmol, 1.1 equiv) in THF (100 ml) cooled to 0° C. The resulting white suspension was diluted with more THF (50 ml) and treated with spiro[4.5]decan-7-one (1) (17.20 g, 113.2 mmol) added dropwise for 20 mn. The reaction mixture was stirred at room temperature for 3 h, treated with saturated $NH_4Cl$ (500 ml) and extracted with MTBE (4×150 ml). The combined organic phases were washed with $H_2O$ (6×70 ml) until neutral pH and dried over $MgSO_4$. 16.90 g (84%) of crude product (2) was isolated as an orange oil that was used without further purification in the following step.

b) 7-(Pent-4-en-1-ynyl)-spiro[4.5]decan-7-ol (3)

To a mixture of KOH (7.93 g), $K_2CO_3$ (1.08 g) and CuCl (0.72 g) in MeOH (40 ml) cooled to 0° C. and kept under $N_2$ was added dropwise a solution of 7-ethynyl-spiro[4.5]decan-7-ol (2) (16.80 g, 94.4 mmol) in iPrOH (40 ml). The resulting red-brown mixture was stirred another 20 minutes at 0° C., then was treated with allylchlorid (11.6 ml, 141.6 mmol, 1.5 equiv) added dropwise for 10 mn, warmed to room temperature and left under stirring at room temperature overnight. The mixture was diluted with MTBE (200 ml), washed with saturated $NH_4Cl$ (2×40 ml), $H_2O$ (3×30 ml) until neutral pH and dried over $MgSO_4$. 18.52 g (90%) of crude product (3) was isolated as an orange oil that was used without further purification in the final step.

c) 1-Spiro[4.5]dec-7-en-7-yl)-pent-4-en-1-one(4) and 1-(spiro[4.5]dec-6-en-7-yl)-pent-4-en-1-one(5)

A solution of 7-(pent-4-en-1-ynyl)-spiro[4.5]decan-7-ol (3) (18.52 g) in $HCO_2H$ 80% (30 ml) was heated at 90° C. under $N_2$ for 58h. The resulting brown mixture was diluted with MTBE (300 ml) and treated with $Na_2CO_3$ 2N (300 ml) added cautiously under stirring. The organic phase was separated, washed with brine (3×100 ml) and dried over $MgSO_4$. After distillation with a Vigreux column, 9.45 g (86–90° C./0.07 Torr) of the product was isolated as a yellow oil. Further purification of a fraction (8.00 g) by flash chromatography on $SiO_2$ (hexane/MTBE 100/1 to 100/2 to 100/3 to 100/4 to 100/5) yielded pure product (yellowish oil) as a mixture of 1-(spiro[4.5]dec-7-en-7-yl)-pent-4-en-1-one (4) and 1-(spiro[4.5]dec-6-en-7-yl)-pent-4-en-1-one (5) in a ratio of 1.8 to 1 (in the crude mixture (4)/(5): 1.3/1).

Both isomers α (4) and β (5) were separated by preparative GLC for $^1$H-NMR analysis.

Odour (mixture (4)/(5): 1.8/1): galbanum, pineapple, metallic.

IR (mixture:(4)+(5), neat): 2936vs, 2858s, 1668vs, 1639s $cm^{-1}$; (vs: very strong; s: strong; m: medium; w: weak).

(4): $^1$H NMR (400 MHz, $CDCl_3$): 6.95–6.89 (1H, m, CH=C), 5.85 (1H, ddt, J 17.2, 10.4, 6.8 Hz, CH=$CH_2$), 5.05 (1H, ddt, J 17.2, 1.6, 1.6 Hz, CH=$CH_2$), 4.99 (1H, ddt, J 10.4, 1.6, 1.2 Hz, CH=$CH_2$), 2.75 (2H, t, J 7.2 Hz, $COCH_2$), 2.42–2.28 (4H, m, —$CH_2$—), 2.17–2.10 (2H, m, $CH_2$), 1.72–1.58 (4H, m, —$CH_2$—), 1.48 (2H, t, J 6.4 Hz, $CH_2$), 1.45–1.30 (4H, m, —$CH_2$—). MS (70 eV): 218 ($M^+$•19), 163 (100), 135 (25), 107 (22), 93 (44), 79 (37), 67 (46), 55 (38), 41 (25).

(5): $^1$H NMR (400 MHz, $CDCl_3$): 6.63 (1H, bs, CH=C), 5.86 (1H, ddt, J 17.2, 10.4, 6.8 Hz, CH=$CH_2$), 5.05 (1H, ddt, J 17.2, 2.0, 1.6 Hz, CH=$CH_2$), 4.98 (1H, ddt, J 10.4, 1.6, 1.2 Hz, CH=$CH_2$), 2.75 (2H, t, J 7.2 Hz, $COCH_2$), 2.42–2.32 (2H, m, $CH_2$), 2.20 (2H, td, J 6.4, 1.6, $CH_2$), 1.80–1.69 (4H, m, —$CH_2$—), 1.67–1.50 (6H, m, —$CH_2$—), 1.50–1.45 (2H, m, $CH_2$). MS (70 eV): 218 (M+•46), 189 (48), 177 (41), 163 (100), 135 (70), 121 (14), 107 (33), 93 (70), 79 (58), 67 (56), 55 (54), 41 (35).

The following examples were all prepared according to the general procedure described for example 1. Only the spectroscopic data and olfactory properties for each example are given below.

EXAMPLE 2

1-Spiro[4.5]dec-2-en-2-yl)-pent-4-en-1-one(6) and 1-(spiro[4.5]dec-1-en-2-yl)-pent-4-en-1-one(7)

Odour (mixture (6)/(7): 1/1.7): pineapple, galbanum, metallic, minty nuances. IR (mixture (6)+(7), neat): 2925vs, 2854s, 1669vs, 1641m, 1617m; (vs: very strong; s: strong; m: medium; w: weak).

(6): $^1$H NMR (400 MHz, $CDCl_3$): 6.64–6.62 (1H, m, CH=C), 5.84 (1H, ddt, J 17.2, 10.4, 6.8 Hz, CH=$CH_2$), 5.05 (1H, ddt, J 17.2, 1.6, 1.6 Hz, CH=$CH_2$), 4.98 (1H, ddt, J 10.4, 2.0, 1.2 Hz, CH=$CH_2$), 2.74 (2H, t, J 7.6 Hz, COCH$_2$), 2.42–2.34 (6H, m, —CH$_2$—), 1.50–1.3 (10H, m, —CH$_2$—). MS (70 eV): 218 (M$^+$•16), 163 (100), 135 (12), 123 (14), 107 (12), 93 (20), 81 (28), 67 (32), 55 (31), 41 (18).

(7): $^1$H NMR (400 MHz, CDCl$_3$): 6.58 (1H, bs, CH=C), 5.85 (1H, ddt, J 17.2, 10.4, 6.8 Hz, CH=CH$_2$), 5.05 (1H, ddt, J 17.2, 1.6, 1.6 Hz, CH=CH$_2$), 4.98 (1H, ddt, J 10.4, 2.0, 1.2 Hz, CH=CH$_2$), 2.75 (2H, t, J 7.2 Hz, COCH$_2$), 2.53 (2H, dt, J 7.2, 1.6 Hz, CH$_2$), 2.40–2.33 (2H, m, CH$_2$), 1.74 (2H, t, J 7.2 Hz, CH$_2$), 1.60–1.35 (10H, m, —CH$_2$—). MS (70 eV): 218 (M$^+$•,18), 189 (17), 177 (10), 163 (100), 135 (10), 107 (26), 93 (20), 79 (20), 67 (18), 55 (25), 41 (12).

EXAMPLE 3

1-(Spiro[4.4]non-2-en-2-yl)-pent-4-en-1-one(8) and 1-(spiro[4.4]non-1-en-2-yl)-pent-4-en-1-one(9)

Odour (mixture (8)/(9): 1/2.5): pineapple, galbanum, metallic. IR (mixture (8)+(9), neat): 2947vs, 2858s, 1668vs, 1613m; (vs: very strong; s: strong; m: medium; w: weak).

(8): $^1$H NMR (400 MHz, CDCl$_3$): 6.71–6.65 (1H, m, CH=C), 5.84 (1H, ddt, J 17.2, 10.4 6.8 Hz, CH=CH$_2$), 5.05 (1H, ddt, J 17.2, 1.6, 1.6 Hz, CH=CH$_2$), 4.98 (1H, ddt, J 10.4, 2.0, 1.2 Hz, CH=CH$_2$), 2.74 (2H, t, J 7.2 Hz, CH$_2$CO), 2.51–2.44 (4H, m, —CH$_2$—), 2.41–2.33 (2H, m, CH$_2$), 1.74–1.46 (8H, m, —CH$_2$—). MS (70 eV): 204 (M$^+$•,10), 175 (5), 149 (100), 131 (8), 121 (9), 105 (7), 93 (16), 79 (17), 67 (7), 55 (9), 44 (10).

(9): $^1$H NMR (400 MHz, CDCl$_3$): 6.54 (1H, bs, CH=C), 5.85 (1H, ddt, J 17.2, 10.4, 6.8 Hz, CH=CH$_2$), 5.05 (1H, ddt, J 17.2, 1.6, 1.6 Hz, CH=CH$_2$), 4.98 (1H, d(bd), J 10.4, 1.6 Hz, CH=CH$_2$), 2.75 (2H, t, J 7.2 Hz, CH$_2$CO), 2.54 (2H, td, J 7.2, 1.6 Hz, CH$_2$), 2.40–2.33 (2H, m, CH$_2$), 1.79 (2H, t, J 7.2 Hz, CH$_2$), 1.75–1.50 (8H, m, —CH$_2$—). MS (70 eV): 204 (M$^+$•,11), 175 (21), 163 (17), 149 (100), 121 (16), 107 (14), 93 (16), 79 (18), 55 (10).

EXAMPLE 4

1-(Spiro[5.5]undec-2-en-2-yl)-pent-4-en-1-one(10) and 1-(spiro[5.5]undec-1-en-2-yl)-pent-4-en-1-one(11)

Odour (mixture (10)/(11): 1.8/1): galbanum, pineapple, metallic, marine. IR (mixture (10)+(11), neat): 2925vs, 2857s, 1669vs, 1640m; (vs: very strong; s: strong; m: medium; w: weak).

(10): $^1$H NMR (400 MHz, CDCl$_3$): 6.88–6.83 (1H, m, CH=C), 5.84 (1H, ddt, J 17.2, 10.4, 6.8 Hz, CH=CH$_2$), 5.03 (1H, ddt, J 17.2, 1.6, 1.2 Hz, CH=CH$_2$), 4.97 (1H, ddt, J 10.4, 1.6, 1.6 Hz, CH=CH$_2$), 2.74 (2H, t, J 7.2 Hz, COCH$_2$), 2.40–2.31 (2H, m, —CH$_2$—), 2.28–2.19 (2H, m, —CH$_2$—), 2.10–2.06 (2H, m, CH$_2$), 1.58–1.34 (8H, m, —CH$_2$—), 1.34–1.18 (4H, m, —CH$_2$—). MS (70 eV): 232 (M$^+$•, 26), 204 (10), 177 (100), 149 (33), 136 (12), 123 (15), 107 (32), 93 (44), 81 (89), 67 (78), 55 (66), 41 (40).

(11): $^1$H NMR (400 MHz, CDCl$_3$): 6.67 (1H, bs, CH=C), 5.85 (1H, ddt, J 17.2, 10.4, 6.8 Hz, CH=CH$_2$), 5.04 (1H, ddt, J 17.2, 2.0, 1.6 Hz, CH=CH$_2$), 4.97 (1H, ddt, J 10.4, 1.6, 1.2 Hz, CH=CH$_2$), 2.74 (2H, t, J 7.2 Hz, COCH$_2$), 2.40–2.31 (2H, m, CH$_2$), 2.19 (2H, td, J 6.4, 1.6, CH$_2$), 1.64–1.32 (14H, m, —CH$_2$—). MS (70 eV): 232 (M$^+$•, 23), 191 (11), 177 (100), 149 (16), 136 (13), 121 (18), 107 (15), 93 (26), 81 (35), 67 (60), 55 (31), 41 (19). EXAMPLE 5

Trans-1-Spiro[4.5]dec7-en-7-yl)-hex-4-en-1-one (12) and trans-1-(spiro[4.5]dec-6-en-7-yl)-hex-4-en-1-one(13)

Odour (mixture (12)/(13): 1.3/1): galbanum, pineapple, metallic. IR (mixture: (12)+(13), neat): 2936vs, 2857s, 1668vs, 1637m cm$^{-1}$ ; (vs: very strong; s: strong; m: medium; w: weak).

(12): $^1$H NMR (400 MHz, CDCl$_3$): 6.91–6.86 (1H, m, CH=C), 5.48–5.42 (2H, m, CH=CH—CH$_3$), 2.68 (2H, t, J 7.2 Hz, COCH$_2$), 2.34–2.24 (4H, m, —CH$_2$—), 2.13–2.09 (2H, m, CH$_2$), 1.72–1.57 (7H, m, —CH$_2$—, CH$_3$), 1.47 (2H, t, J 6.4 Hz, CH$_2$), 1.42–1.31 (4H, m, —CH$_2$—). MS (70 eV): 232 (M$^+$, 18), 203 (10), 163 (100), 135 (10), 107 (16), 93 (20), 79 (15), 67 (14), 55 (10), 41 (10).

(13): $^1$H NMR (400 MHz, CDCl$_3$): 6.60 (1H, bs, CH=C), 5.48–5.42 (2H, CH=CH—CH$_3$), 2.68 (2H, t, J 7.2 Hz, COCH$_2$), 2.32–2.24 (2H, m, CH$_2$), 2.18 (2H, td, J 6.4, 1.6, CH$_2$), 1.76–1.69 (4H, m, —CH$_2$—), 1.66–1.50 (9H, m, —CH$_2$—, CH$_3$), 1.49–1.42 (2H, m, CH$_2$). MS (70 eV): 232 (M$^+$, 34), 203 (37), 189 (18), 177 (35), 163 (100), 150 (16), 135 (42), 121 (11), 107 (20), 93 (42), 79 (29), 67 (22), 55 (17), 41 (15).

EXAMPLE 6

| Green-ambery masculine accord | parts per weight |
|---|---|
| α-Hexyl cinnamic aldehyde | 70 |
| Aldehyde C12 MNA pure (2-methylundecanal) | 1 |
| Ambroxan (3a-methyl-dodecahydro-6,6,9a-trimethylnaphto [2,1-b]furan | 2 |
| Basil oil | 2 |
| Bergamot oil Abergapt | 100 |
| Gaiac wood oil | 40 |
| Cepionate (methyl dihydrojasmonate) | 100 |
| Coumarine (pure crist.) | 20 |
| Cyclohexal (4-(4-hydroxy-4-methylpentyl)-cyclohex-3-en-1-carboxaldehyde) | 20 |
| Dimetol (2,6-Dimethyl-2-heptanol) | 80 |
| Dipropylene glycol | 22 |
| Ebanol ® (Givaudan Roure) | 30 |
| Frankincense ess. pure | 2 |
| Evernyl ® (Givaudan Roure) | 10 |
| Oxyoctaline formate (2,5,9,10-tetramethyl-5,6-dehydrodecalyl formate) | 120 |
| Galbanum oil conc. | 2 |
| Geranium Oil Africa | 15 |
| Hydrocarboresine SB | 1 |
| Kephalis (4-(1-ethoxyethenyl)-3,3,5,5-tetra-methyl-cyclohexanone) | 50 |
| Lavandin super pur clle | 20 |
| Lilial ® (Givaudan Roure) | 20 |
| Nectaryl (2-(2-(4-methyl-3-cyclohexen-1-yl) propyl)-cyclopentanone | 8 |
| Nutmeg oil. | 10 |
| Patchouli ess. sans fer | 30 |
| Sandalore ® (Givaudan Roure) | 60 |
| Compound of example 1 | 2 |
| Thibetolide ® (Givaudan Roure) | 150 |
| Tricyclal (2,4-dimethyl-3-cyclohexene-carboxaldehyde) | 1 |
| Tropional (α:-methyl-1,3-benzodioxole-5-propanal) | 10 |
| Vetiver oil Haiti | 2 |
| Total: | 1000 |

The novel compound has a remarkable synergistic effect with the green, woody notes of this masculine accord. It brings volume, diffusion to the composition together with a unique green, fruity and fresh vibration. This effect is long lasting and develops over time.

EXAMPLE 7

| Cologne composition for powder detergent | |
|---|---|
| | parts per weight |
| 2-Isobutyl-3-methoxy pyrazine DB (10% DPG) | 1 |
| Compound of example 1 (10% DPG) | 4 |
| Gardenol (1-phenylethyl acetate) | 5 |
| Undecatriene (10% in DPG) | 5 |
| Lemonile (3,7-dimethyl-2,6-nona-diene-nitrile) | 5 |
| Stemone ® (Givaudan Roure) | 5 |
| Methyl salicylate | 5 |
| Methyl anthranilate | 10 |
| Indole (10% in DPG) | 10 |
| 2-Methoxynaphtalene | 20 |
| Orange Oil | 35 |
| 2-Ethoxynaphtalene | 45 |
| Benzyl acetone | 50 |
| Ebanol ® (Givaudan Roure) | 50 |
| Terpinyl acetate | 100 |
| Lilial ® (Givaudan Roure) | 100 |
| Tetrahydrolinalool | 250 |
| α-Hexyl cinnamic aldehyde | 300 |
| Total: | 1000 |

The novel compound enhances the fresh, floral, green note of the perfumed product. It adds volume, diffusion and longlastingness to the clean and fresh note of the product.

EXAMPLE 8

| Fresh floral composition for liquid detergent | |
|---|---|
| | parts per weight |
| Lilial ® (Givaudan Roure) | 200 |
| 4-(1,1-dimethylethyl)cyclohexyl acetate | 50 |
| Ebanol ® (Givaudan Roure) | 2 |
| Dihydromyrcenol | 50 |
| Linalool (synth.) | 50 |
| Terpineol pure | 100 |
| Verdyl acetate (4,7-methano-1H-3a,4,5,6,7,7a-hexahydroinden-6-yl acetate) | 60 |
| Verdyl propionate (4,7-methano-1H-3a,4,5,6,7,7a-hexahydroinden-6-yl propionate) | 60 |
| α-Hexyl cinnamic aldehyde | 130 |
| Fixolide ® (Givaudan Roure) | 100 |
| Citronellol extra | 100 |
| Dipropylene glycol | 68 |
| Compound of example 1 | 30 |
| Total: | 1000 |

The novel compound gives greater intensity, volume and freshness to the perfumed product. This fresh and clean note remains remarkably present on wet and dry fabrics washed with the detergent that reflects high substantivity of the new molecule.

The systematic chemical names of the trivial names of the individual components mentioned above are listed in stardard works, e.g. Flavour and Fragrance Materials 1996, Allured Publishing Corporation, Carol Stream, Ill., U.S.A. or Arctander, Perfume and Flavor Chemicals—1969, published by the author, Montclair, N.J., U.S.A.

While the invention has been described with respect to illustrative embodiments and modes of practice, it will be apparent to those skilled in the art that various modifications and improvements may be made without departing from the scope of the present invention.

What is claimed is:

1. A compound of the general formula (I):

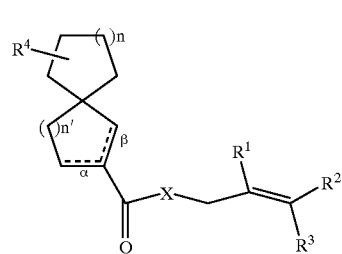

(I)

in which the —C(O)X-substituted ring is saturated or unsaturated in the α or β position and wherein:

X represents a methylene group or an oxygen atom, $R^1$, $R^2$, $R^3$, $R^4$ are independently a hydrogen atom or a methyl radical, n and n' are independently 1 or 2, $R^4$ is at any position on the ring.

2. The compound according to claim 1, wherein the compound is an α-isomer.

3. The compound according to claim 1, wherein the compound is a β-isomer.

4. The compound according to claim 1, taken from the group consisting of 1-(spiro[4.5]dec-7-en-7-yl)-pent-4-en-1-one and 1-(spiro[4.5]dec-6-en-7-yl)-pent-4-en-1-one.

5. The compound according to claim 1, taken from the group consisting of 1-(spiro[4.5]dec-2-en-2-yl)-pent-4-en-1-one and 1-(spiro[4.5]dec-1-en-2-yl)-pent-4-en-1-one.

6. The compound according to claim 1, taken from the group consisting of 1-(spiro[4.4]non-2-en-2-yl)-pent-4-en-1-one and 1-(spiro [4.4]non-1-en-2-yl)-pent-4-en-1-one.

7. The compound according to claim 1, taken from the group consisting of 1-(spiro[5.5]undec-2-en-2-yl)-pent-4-en-1-one and 1-(spiro[5.5]undec-1-en-2-yl)-pent-4-en-1-one.

8. The compound according to claim 1, taken from the group consisting of trans-1-(spiro[4.5]dec-7-en-7-yl)-hex-4-en-1-one and trans-1-(spiro[4.5]dec-6-en-7-yl)-hex-4-en-1-one.

9. A perfume composition comprising at least one compound of general formula (I):

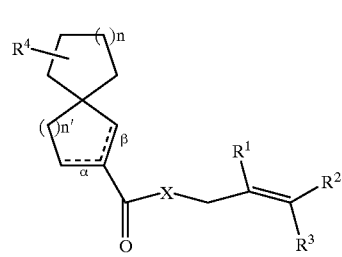

(I)

in which the —C(O)X-substituted ring is saturated or unsaturated in the α or β position and wherein:

X represents a methylene group or an oxygen atom, $R^1$, $R^2$, $R^3$, $R^4$ are independently a hydrogen atom or a methyl radical, n and n' are independently 1 or 2, $R^4$ is at any position on the ring.

10. A perfume composition comprising at least one compound taken from the group consisting of 1-(spiro[4.5]dec-7-en-7-yl)-pent-4-en-1-one; 1-(spiro[4.5]dec-6-en-7-yl)-pent-4-en-1-one; 1-(spiro[4.5]dec-2-en-2-yl)-pent-4-en-1-one; 1-(spiro[4.5]dec-1-en-2-yl)-pent-4-en-1-one; 1-(spiro[4.4]non-2-en-2-yl)-pent-4-en-1-one; 1-(spiro[4.4]non-1-en-2-yl)-pent-4-en-1-one; 1-(spiro[5.5]undec-2-en-2-yl)-pent-4-en-1-one; 1-(spiro[5.5]undec-1-en-2-yl)-pent-4-en-1-one; trans-1-(spiro[4.5]dec-7-en-7-yl)-hex-4-en-1-one; and trans-1-(spiro[4.5]dec-6-en-7-yl)-hex-4-en-1-one.

* * * * *